(12) United States Patent
Conway

(10) Patent No.: US 8,419,690 B2
(45) Date of Patent: Apr. 16, 2013

(54) MEDICAL DEVICE WITH NEEDLE SAFETY SHIELDING

(75) Inventor: Hugh T. Conway, Verona, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1758 days.

(21) Appl. No.: 11/465,157

(22) Filed: Aug. 17, 2006

(65) Prior Publication Data

US 2007/0060840 A1   Mar. 15, 2007

Related U.S. Application Data

(60) Provisional application No. 60/709,151, filed on Aug. 18, 2005.

(51) Int. Cl.
*A61M 5/32* (2006.01)

(52) U.S. Cl.
USPC .......................... 604/192; 604/198; 604/110

(58) Field of Classification Search .................. 604/110, 604/192, 263, 171, 177
See application file for complete search history.

(56) References Cited

U.S. PATENT DOCUMENTS

| 5,330,438 | A | * | 7/1994 | Gollobin et al. | 604/177 |
| 5,403,286 | A | * | 4/1995 | Lockwood, Jr. | 604/110 |
| 5,746,215 | A | * | 5/1998 | Manjarrez | 600/573 |
| 6,641,555 | B1 | * | 11/2003 | Botich et al. | 604/110 |
| 2003/0163096 | A1 | | 8/2003 | Swenson et al. | |
| 2004/0162523 | A1 | | 8/2004 | Conway | |

FOREIGN PATENT DOCUMENTS

| EP | 0356002 A2 | 2/1990 |
| WO | 02087672 A | 11/2002 |

* cited by examiner

*Primary Examiner* — Laura Bouchelle
(74) *Attorney, Agent, or Firm* — The Webb Law Firm

(57) ABSTRACT

In one aspect, a medical device is provided which includes flexible tubing having a distal end and a proximal end and at least a first lumen extending from said distal end to said proximal end; a first needle cannula having proximal and distal ends, said first needle cannula being mounted at said distal end of said tubing and in fluid communication with said lumen; a second needle cannula mounted at said proximal end of said tubing and in fluid communication with said lumen; a shield disposed over said tubing, said shield extending substantially the entire length of said flexible tubing, and said shield being movable relative to said first needle cannula from an initial proximal position wherein said first needle cannula is exposed to a distal position wherein said distal end of said first needle cannula is covered by said shield; and an actuator for actuating the shield at a location spaced from the first needle cannula, preferably closer to the second needle cannula than to the first needle cannula.

21 Claims, 9 Drawing Sheets

MEDICAL DEVICE WITH NEEDLE SAFETY SHIELDING

CROSS-REFERENCE TO RELATED APPLICATIONS

This application is claiming the benefit under 35 U.S.C. 119(e) to Provisional Application Ser. No. 60/709,151, filed Aug. 18, 2005 which is herein incorporated by reference.

FIELD OF THE INVENTION

This invention relates to needle safety shielding for preventing inadvertent needle contact and, more particularly, to needle safety shielding for medical devices, such as blood collection sets, infusion sets, or fluid administration sets.

DESCRIPTION OF THE PRIOR ART

Blood collection sets are known in the prior art, wherein an Intravenous (IV) needle cannula is provided for insertion into a patient's blood vessel with the IV cannula secured to an IV hub, as can be seen in U.S. Pat. No. 5,951,525 to Thome et al for example, and a flexible tube extending from the IV hub to a second cannula, onto which is typically mounted a needle holder. The second cannula is used to pierce the septum of an evacuated blood collection tube or blood bag so that blood is transferred thereinto via the two cannulae and the connecting tube. The septum is typically a resealable pierceable elastomeric stopper.

As with most, if not all, sharp medical devices which are inserted into a patient (e.g., syringes; catheters; scalpels), inadvertent "sticks" by a needle cannula of a blood collection set into a practitioner post patient-insertion have become a major health concern, particularly with respect to the transmission of blood-borne diseases (e.g., HIV). Various needle shielding and capping devices have been developed in the prior art to wholly, or at least partially, encapsulate used needle cannulae and prevent inadvertent contact therewith. Many of these devices require additional effort by a practitioner to be practiced, ranging from slipping a cap over the used needle cannula to activating a mechanism that drives a shield about the needle cannula.

While the benefits of such shielding and capping devices are apparent, such devices can in some cases contain relatively bulky, rigid components and mechanisms in the area of the IV cannula hub. These components and mechanisms generally add weight, sometimes obstruct vision and may also act undesirably against the skin, all of which may contribute to the IV cannula having an upwards rotation force element while in the vein, which may cause pain and/or necessitate securement of the device against the skin. These potential drawbacks are amplified when the device is used on a small child, infant or premature baby. These negative aspects may detract from the utility of such devices and can cause some phlebotomists to select alternative medical devices without safety features.

Devices having the functional and safety features of existing devices, but without the potential drawbacks noted above, would therefore be desirable.

SUMMARY OF THE INVENTION

In one aspect, the invention is a medical device which includes flexible tubing having a distal end and a proximal end and at least a first lumen extending from said distal end to said proximal end; a first needle cannula having proximal and distal ends, said first needle cannula being mounted at said distal end of said tubing and in fluid communication with said lumen; a second needle cannula mounted at said proximal end of said tubing and in fluid communication with said lumen; a shield disposed over said tubing, said shield extending substantially the entire length of said flexible tubing, and said shield being movable relative to said first needle cannula from an initial proximal position wherein said first needle cannula is exposed to a distal position wherein said distal end of said first needle cannula is covered by said shield. Typically, the device further has an actuator for actuating the shield at a location spaced from the first needle cannula, preferably closer to the second needle cannula than to the first needle cannula.

According to embodiments of the invention, passive or manual activation of a safety shield can be achieved. With passive activation, no additional effort outside of normal operation of the medical device is necessary to cause needle shielding. If desired, manual activation of the safety shield can be provided as an alternative, or in addition, to passive activation. The invention is applicable to various medical devices, but is particularly well-suited for intravenous infusion sets and blood collection sets. For illustrative purposes, discussion herein will relate to embodiments directed to blood collection sets.

These and other features of the invention will be understood through a study of the following detailed description and accompanying drawings.

DETAILED DESCRIPTION OF THE INVENTION

Figure 1:
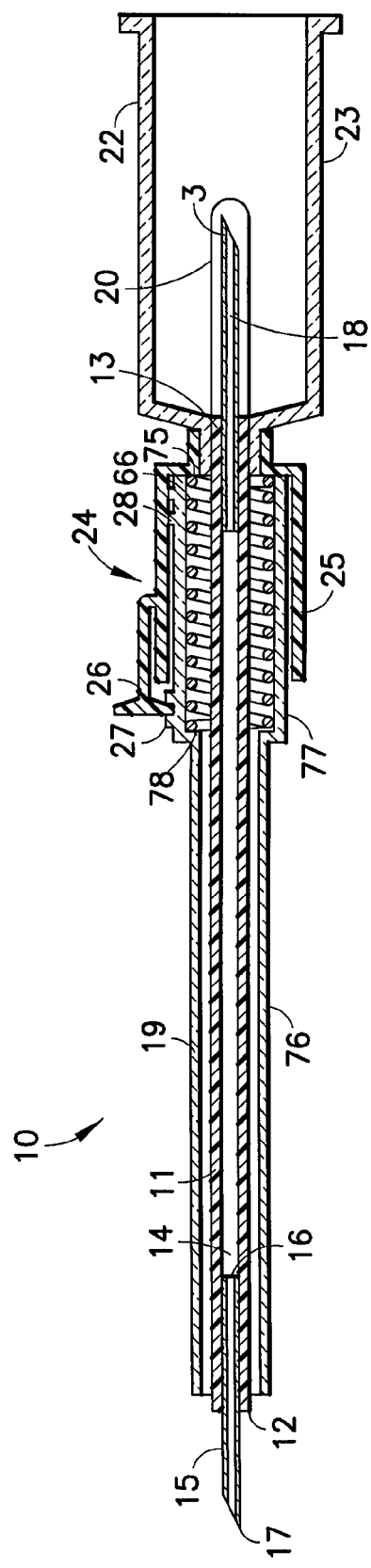
FIG. 1 is a cross-sectional view of one embodiment of the invention.
Figure 4:
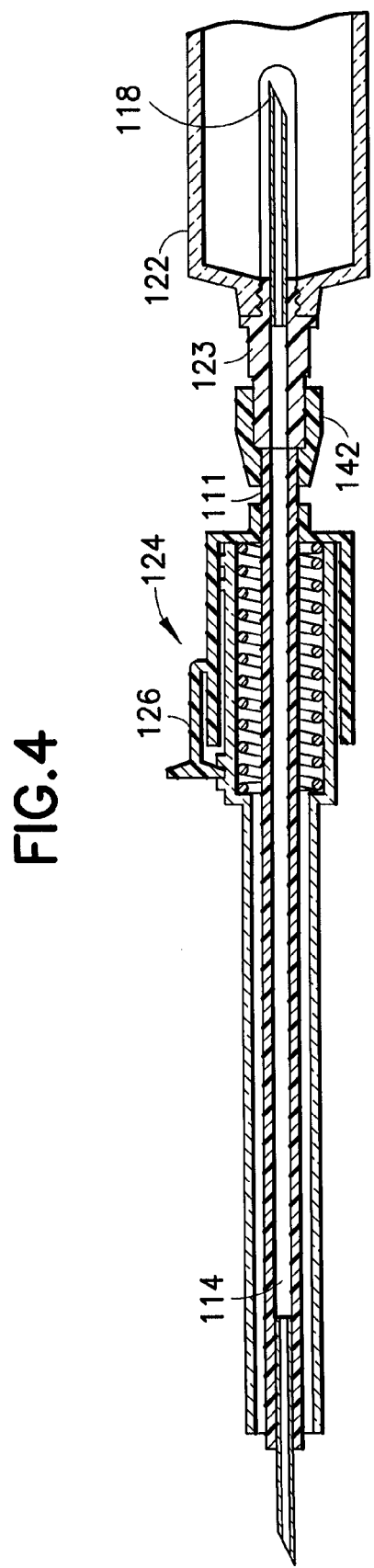
FIG. 4 is a cross-sectional side view of the female to male luer interface in an embodiment of the invention.

According to an embodiment of the invention, with reference to FIGS. 1-4, a medical device 10 is depicted (as shown therein, a blood collection set), which generally includes;

Flexible tubing 11, having a distal end 12 and a proximal end 13 and a first lumen 14 for communicating the first and second needle cannulae 15 and 18. Typically the flexible tubing has an outside diameter of 1 centimeter or less and is easily flexed or bent along the longitudinal axis of the tubing by a user or by the weight of the device itself. The tubing 11 may be fixed to the first and second needle cannulae 15 and 18 using any technique known to those skilled in the art. In the embodiment of FIG. 1, the first and second cannulae are directly bonded to the flexible tubing 11 with a suitable adhesive. FIG. 4 shows an alternative embodiment in which tubing 11 is bonded indirectly to the second needle cannula 18 by additional mating elements such as a luer 142 and a non-patient needle hub 123. Advantageously, as reflected in the embodiments of FIGS. 1, 4, 5 and 7 there is no IV cannula needle hub, thereby reducing the weight and bulk of the IV end of the blood collection set of the invention when compared to traditional blood collection set designs.

The needle cannulae 15 and 18 are formed in any known fashion such as by drawn metal tubes or molded elastomers. The first needle cannula 15 includes a sharp distal end 17 for insertion into a patient and a proximal end 16. A proximal end 3 of the second needle cannula 18 may also be sharp to facilitate piercing of a septum of a blood collection device (e.g., evacuated blood collection tube; blood bag). The second needle cannula 18 may also be ensheathed in a compressible elastomeric sleeve 20, which acts to seal the proximal end 3 of the cannula 18 from leakage, e.g., in the case of multiple sample containers such as multiple evacuated tubes, as known in the art. Both needle cannulae 15 and 18 are formed hollow and are fluid communication with each other via the first lumen 14. For example, when the second needle cannula 16 is inserted into an evacuated blood collection device, the vacuum therein draws blood through the first needle cannula 15, the lumen 14, and the second needle cannula 18 and into the blood collection device.

At least one wing 21 may be attached to the shield 19. The wing may be used for gripping during insertion and/or for securing the blood collection set to a patient during collection. Advantageously, the wing or wings 21 are formed from a thin flexible thermoplastic material that provides sufficient surface area for gripping by a user and/or securement to the patient's skin, but at a reduced bulk and weight at relative to conventional blood collection sets. Suitable materials for such wings include Poly Vinyl Chloride, Polyamide, Polypropylene or Polyethylene. Alternate materials for such wings may include thin flexible non-thermoplastic materials such as paper.

Figure 2:
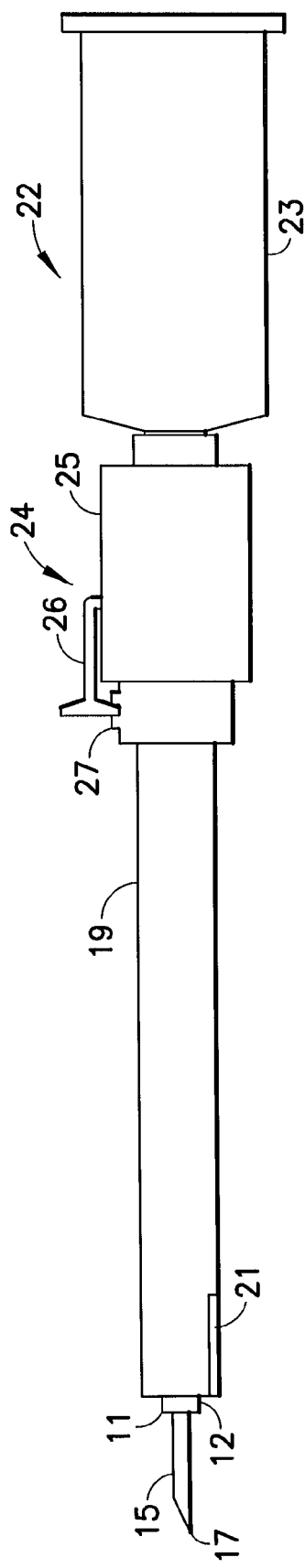
FIG. 2 is a perspective view of the embodiment of FIG. 1 with the shield in the proximal position.
Figure 3:
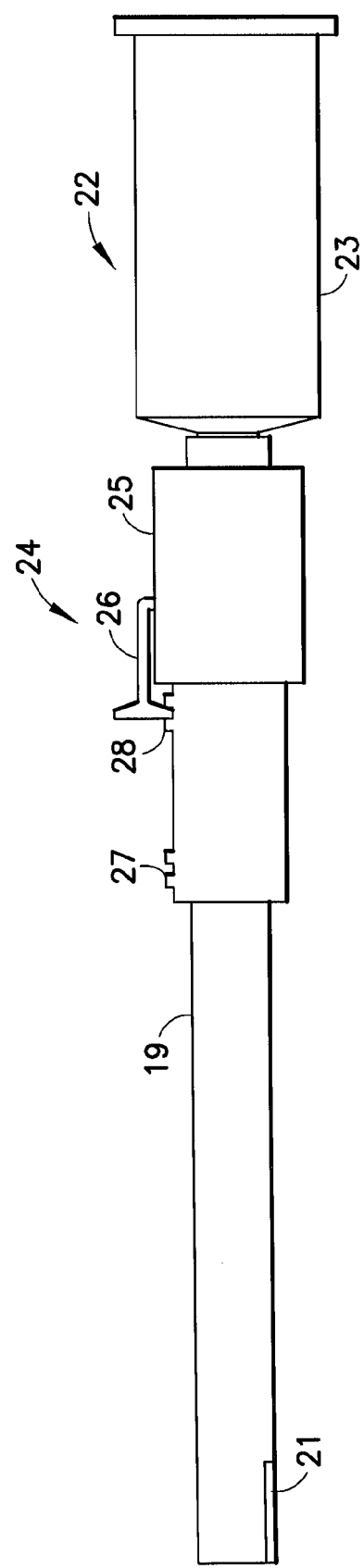
FIG. 3 is a perspective view of the embodiment of FIG. 1 with the shield in the distal position.

The embodiment of FIGS. 1 to 3 includes a needle holder 22 to which the flexible tubing 11 is mounted directly by bonding. As known in the art, the needle holder 22 generally provides a cylindrical body 23 formed to accommodate an evacuated blood collection tube (not shown) and a forward end/fitting/region adapted to accommodate a needle cannula for piercing the septum of a collection device. FIG. 4 shows another embodiment wherein the second needle cannula 118 is secured to a non-patient needle hub 123 that is in turn secured to the needle holder 122. The non-patient needle hub 123 is shown in FIG. 4 with a threaded connection, but other securement techniques are also possible, e.g., a snap-fit connection. According to the embodiment of FIG. 4, the flexible tubing 111 is bonded to a luer 142 mounted onto the non-patient needle hub 123 of the needle holder 122.

Figure 8:
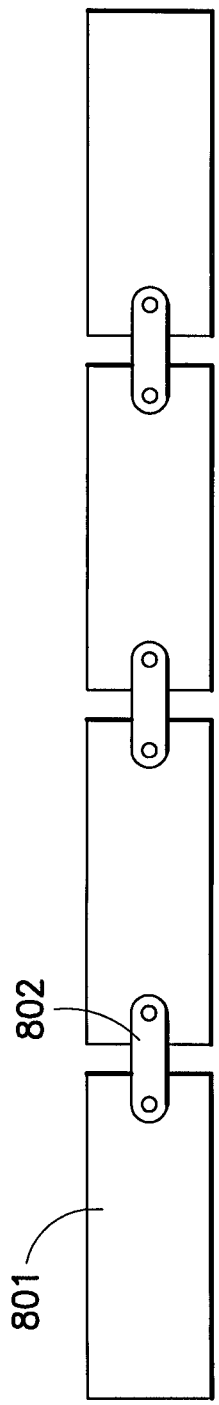
FIG. 8 is a perspective view of a shield in an embodiment of the invention.
Figure 9:
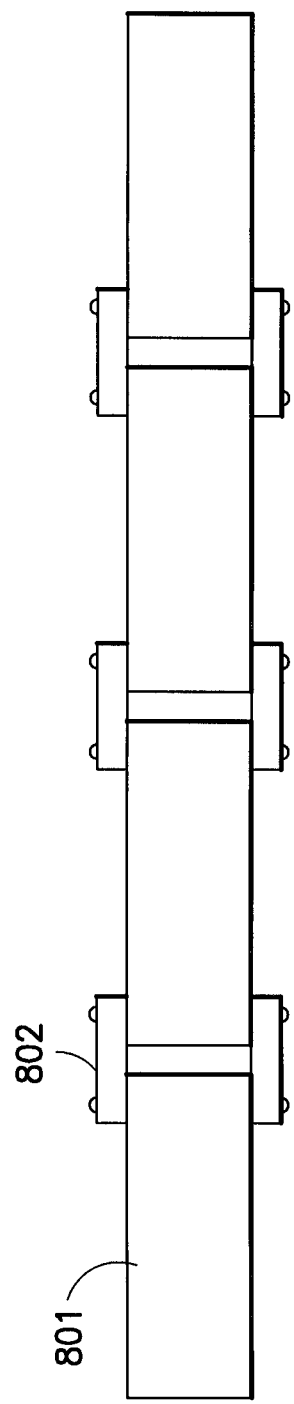
FIG. 9 is a side elevation view of the embodiment of FIG. 8.
Figure 10:
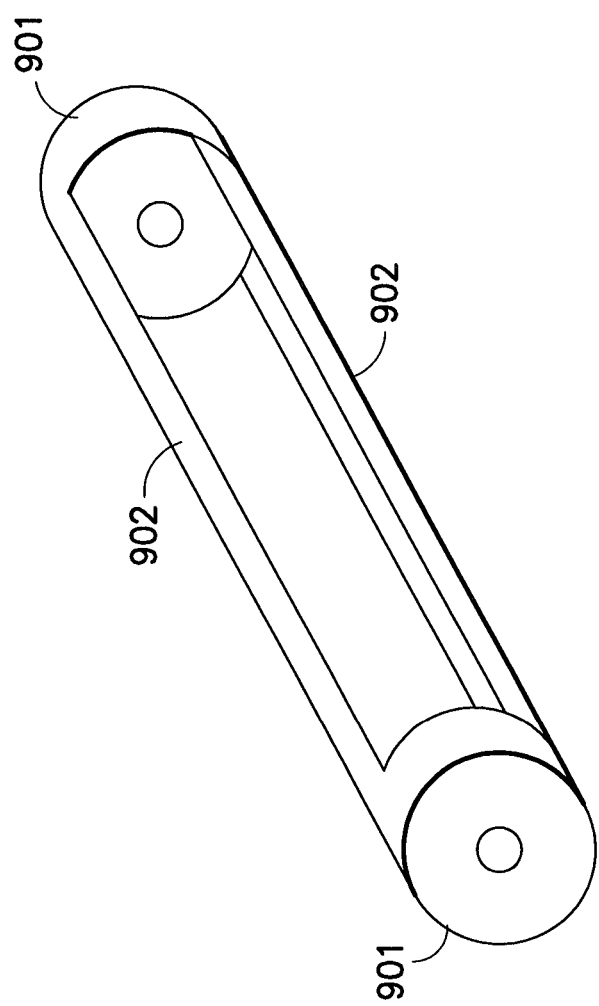
FIG. 10 is a side elevation view of a shield in an embodiment of the invention.

According to an embodiment of the invention, the shield 19 is disposed over the flexible tubing 11, and extends substantially the entire length of the flexible tubing 11. Typically, the shield length will be at least 80% of the entire length of the tubing, more typically at least 90%, and advantageously at least 95%. The shield may be formed from any suitable material such as thermoplastic polymers, elastomers or metallic mesh. The shield may have a variety of configurations. It may be for example, a continuous solid along its length that is formed as a single component or as separate multiple components that are joined together (as in the embodiments of FIGS. 1 to 6) or may be discontinuous e.g., a series of interconnected links or segments 801 which are joined by a series of hinges 802 (as shown from above in FIG. 8 and from the side in FIG. 9), or configured with tubular elements 901 at either end thereof (to provide shielding and actuation function) connected by one or more linear lengths 902 (as shown in FIG. 10). Generally, the shield is disposed telescopically over the tubing.

A shield drive mechanism 24 is typically provided to move the shield 19 relative to said first needle cannula 15 from an initial proximal position (See FIG. 2) wherein said first needle cannula 15 is exposed, to a distal position (See FIG. 3) wherein said distal end 17 of said first needle cannula is covered by said shield 19. The shield drive mechanism 24 may be of any design which causes relative movement between the shield 19 and the first needle cannula 15 in urging the shield 19 into a distal position covering the first needle cannula 15. The shield drive mechanism may include, for example, a bias element such as a spring 66, or elements to facilitate or simply allow manual movement of the shield.

In the embodiments of FIGS. 1-4, the safety shield requires manual activation. The shield drive mechanism 24 includes a bias element (spring 66), a housing 25, an actuator (a resilient latch 26), a proximal position locking member 27 and a distal position locking member 28. The shield 19 has 2 regions of different cross section. The first region 76 has a cross section which encompasses the flexible tubing 11 but is smaller than the internal diameter of the spring 66, while the second region 77 has a cross section that is larger than the outer diameter of the spring. The second region 77 of the shield thus encompasses both the spring 66 as well as tubing 11 and is located within the housing 25 when the shield 19 is in the proximal position. An annular wall 78 is formed at the interface of the two regions of different cross section of the shield 19. Spring 66 is located between the outer surface of flexible tubing 11 and the shield 19; the proximal end of the spring 66 is retained against the proximal wall 75 of the housing 25 while the distal end of the spring 66 exerts the urging force on the annular wall 78. The shield is retained in the proximal position by the interaction between the resilient latch 26 and the proximal position locking member 27. The resilient latch 26 has an inherent positive bias towards engagement with the proximal position locking member 27 when the shield is in the proximal position and with the distal position locking member 28 when the shield is in the distal position. Removal of the latch 26 from the proximal position locking member 27 by the user, is effected by lifting the latch 26 out of engagement with the proximal position locking member 27, which allows spring 66 to drive the relative movement between the first needle cannula 15 and the shield 19 in a distal direction from the proximal position to the distal position. The distal movement of the shield 19 is arrested at the distal position by the engagement of the actuator 26 in the distal position locking member 28, through the inherent positive bias of the latch as described above. The shield 19 is then locked in the distal position.

Figure 5:
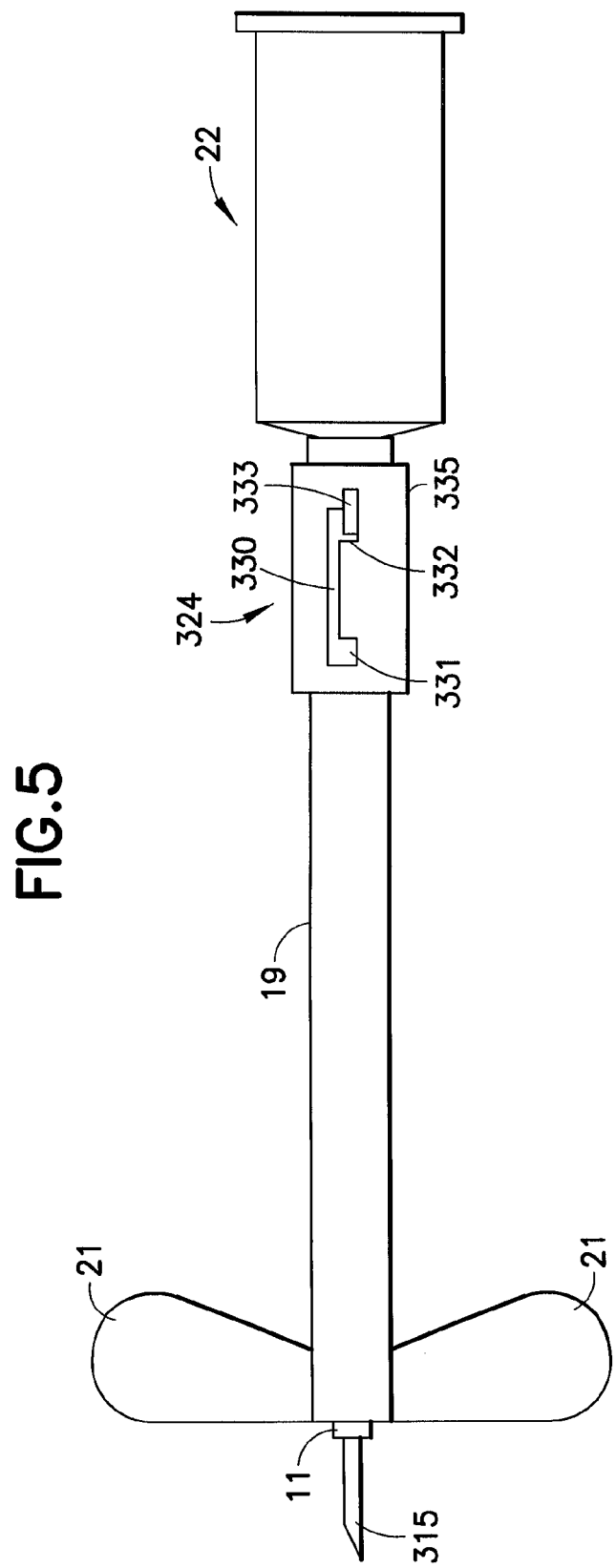
FIG. 5 is a perspective view of another embodiment of the invention.
Figure 6:
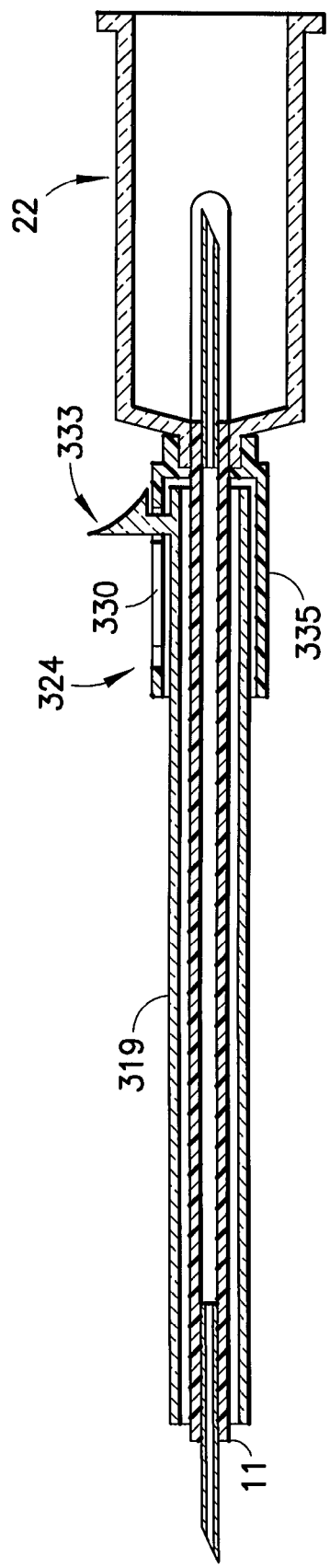
FIG. 6 is a cross-sectional side elevation view of the embodiment of FIG. 5.

The embodiment of FIGS. 5 and 6, show another type of shield drive 324. This mechanism is a manual shield drive mechanism 324 in which the actuator (a finger grip 333) is manipulated by the user's hand and physically moved to actuate shielding. Actuator 333 is located in proximal stop 332 of housing 335 before use thereby securing the shield 319 in the proximal position. After or during collection of the blood sample, the actuator 333 is manually manipulated out of proximal stop 332 and along slot 330 in housing 335 in a distal direction, and into distal stop 331 thereby advancing the shield over the IV needle cannula 315 and securing it in the distal position.

Figure 7:
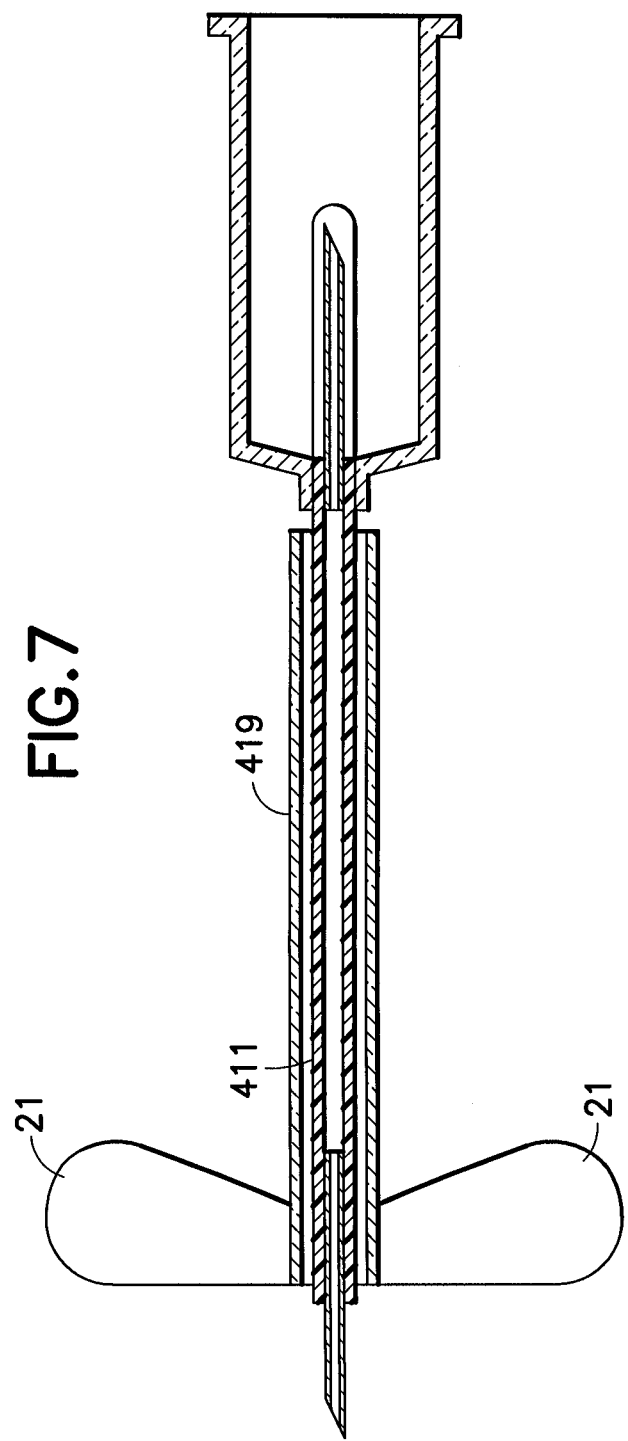
FIG. 7 is a perspective view of another embodiment of the invention.

FIG. 7 shows another embodiment which uses manual manipulation to effect needle shielding. The user grips the shield 419 at any point along its length and physically pushes the shield in a distal direction from the proximal position to the distal position along the tubing 411. In this embodiment, the shield drive mechanism is therefore the shield exterior and does not contain, or require an actuator however at least one latch (not shown) maybe present to retain the shield 419 in the proximal position and distal position.

The actuator, if present, can be a push button, a latch or a finger grip, for example, is used to actuate the shield drive mechanism through either manual or passive activation. A push button is any element that effects actuation of the shield drive mechanism via a pushing force. A latch is any element that effects actuation of the shield drive mechanism by disengaging an element from a retaining feature such as a notch, hole, or lug. Note that an example of a latch 26/126 is shown in FIGS. 1-4. A finger grip is any element that effects actuation of the shield drive mechanism by translating force from one or more of a users' digits to the shield. FIGS. 1 to 6 show that the location of an actuator is typically spaced from the first needle cannula. However the actuator can be located anywhere along the length of the shield particularly for a manually activated safety shield, but it is advantageous for the actuator to be located closer to the second needle cannula than to the first needle cannula. If a bias element is present in the shield drive mechanism, the actuator will typically be located closer to the second cannula.

Another embodiment uses passive activation to effect needle shielding. An actuator is provided for releasing the shield from the proximal position and enabling a biasing element to propel the shield to the distal position. The actuator may be actuated automatically and passively in response to an operational condition indicative of use of the blood collection set. For example, the blood collection set intended for use with an evacuated tube may have an actuator located through the distal wall of the needle holder, which is actuates the shield drive mechanism by the movement of an evacuated tube into communication with the proximal end of the needle cannula. As can be seen in U.S. patent application Ser. No. 10/369,790 to Conway for example.

As will be readily recognized by those skilled in the art, any design or configuration can be used to translate manual or passive activation of the safety shield into movement of the shield.

While the invention has been described in relation to the preferred embodiments with several examples, it will be understood by those skilled in the art that various changes may be made without deviating from the spirit and scope of the invention as defined in the appended claims.

What is claimed is:

1. A medical device comprising;
   flexible tubing having a distal end and a proximal end and at least a first lumen extending from said distal end to said proximal end;
   a first needle cannula having proximal and distal ends, said first needle cannula being mounted at said distal end of said tubing and in fluid communication with said lumen;
   a second needle cannula mounted at said proximal end of said tubing and in fluid communication with said lumen;
   a shield disposed over said tubing, said shield extending substantially the entire length of said flexible tubing, and said shield being movable relative to said first needle cannula from an initial proximal position wherein said distal end of said first needle cannula is exposed to a distal position wherein said distal end of said first needle cannula is covered by said shield.

2. A device as in claim 1, wherein said shield is movable from said proximal position to said distal position via manual manipulation of said shield.

3. A device as in claim 1, further comprising;
   a shield drive mechanism
   wherein said shield is moved from said proximal position to said distal position by said shield drive mechanism.

4. A device as in claim 3, wherein said shield drive mechanism comprises;
   an actuator.

5. A device as in claim 4, wherein said actuator is located closer to said second needle cannula than said first needle cannula.

6. A device as in claim 3, wherein said shield drive mechanism comprises
   a housing and
   a spring for propelling said shield from said proximal position toward said distal position.

7. A device as in claim 6, wherein said spring is disposed at the proximal end of said shield.

8. A device as in claim 3, wherein said shield drive mechanism is disposed at the proximal end of said shield.

9. A device as in claim 1, further comprising at least one wing.

10. A device as in claim 9, wherein said wing is attached to said shield.

11. A device as in claim 9, wherein said wing is made from a thermoplastic material.

12. A device as in claim 1 further comprising a needle holder engaged with said flexible tubing.

13. A device as in claim 1 further comprising a needle holder engaged with said second needle cannula.

14. A device as in claim 1, wherein said shield is telescoped over said flexible tubing such that said shield moves in a distal direction relative to said flexible tubing on movement from said proximal position to said distal position.

15. A device as in claim 1, wherein said shield has a tubular solid cross section.

16. A device as in claim 1, wherein said shield has a segmented composition.

17. A device as in claim 1, wherein said shield has a length greater than 80% of the length of said flexible tubing.

18. A device as in claim 1, wherein said shield has a length greater than 90% of the length of said flexible tubing.

19. A device as in claim 1, wherein said shield has a length greater than 95% of the length of said flexible tubing.

20. A medical device consisting essentially of:
    flexible tubing having a distal end and a proximal end and at least a first lumen extending from said distal end to said proximal end;
    a first needle cannula having proximal and distal ends, said first needle cannula being mounted at said distal end of said tubing and in fluid communication with said lumen;
    a second needle cannula mounted at said proximal end of said tubing and in fluid communication with said lumen;
    a shield disposed over said tubing, said shield extending substantially the entire length of said flexible tubing, and said shield being movable relative to said first needle cannula from an initial proximal position wherein said first needle cannula is exposed to a distal position wherein said distal end of said first needle cannula is covered by said shield;
    an actuator for effecting said movement of said shield, wherein said actuator is selected from the group consisting of a push button, a latch and a finger grip; and
    at least one wing attached to said medical device.

21. A blood collection set consisting essentially of:
    flexible tubing having a distal end and a proximal end and at least a first lumen extending from said distal end to said proximal end;

a first needle cannula having proximal and distal ends, said first needle cannula being mounted at said distal end of said tubing and in fluid communication with said lumen;

a second needle cannula mounted at said proximal end of said tubing and in fluid communication with said lumen;

a shield disposed over said tubing, said shield extending substantially the entire length of said flexible tubing, and said shield being movable relative to said first needle cannula from an initial proximal position wherein said first needle cannula is exposed to a distal position wherein said distal end of said first needle cannula is covered by said shield;

a shield drive mechanism wherein said shield is moved from said proximal position to said distal position by said shield drive mechanism; and at least one wing attached to said medical device.

* * * * *